United States Patent [19]

Jalkian et al.

[11] Patent Number: 5,304,522
[45] Date of Patent: Apr. 19, 1994

[54] LIQUID ACID REGENERATION METHOD

[75] Inventors: Rafi Jalkian, Mantua; Tomas R. Melli, Sewell, both of N.J.

[73] Assignee: Mobil Oil Corporation, Fairfax, Va.

[21] Appl. No.: 69,486

[22] Filed: Jun. 1, 1993

[51] Int. Cl.$^5$ .............. B01J 20/34; B01D 15/04; C01B 7/19; C07C 2/60
[52] U.S. Cl. .................. 502/22; 210/690; 210/692; 423/484; 423/488; 502/31; 585/709; 585/723; 585/724
[58] Field of Search .............. 502/22, 31; 210/690, 210/692; 423/484, 488; 585/723, 724, 730, 809

[56] References Cited

U.S. PATENT DOCUMENTS

| | | | |
|---|---|---|---|
| 2,541,044 | 2/1951 | Daugherty | 502/31 |
| 3,778,489 | 12/1973 | Parker et al. | 260/683.43 |
| 3,794,691 | 2/1974 | Dixon et al. | 585/718 |
| 3,795,712 | 3/1974 | Torck et al. | 260/671 C |
| 3,856,764 | 12/1974 | Throckmorton et al. | 260/82.1 |
| 3,871,969 | 3/1975 | Chapman | 423/488 |
| 4,014,953 | 3/1977 | Brown, Jr. | 585/718 |
| 4,025,577 | 5/1977 | Siskin et al. | 260/683.51 |
| 4,099,924 | 7/1978 | Berkman et al. | 23/273 SP |
| 4,199,409 | 4/1980 | Skraba | 585/723 |
| 4,423,277 | 12/1983 | Stroud | 585/719 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |
| 5,191,150 | 3/1993 | Child et al. | 585/809 |
| 5,237,122 | 8/1993 | Eastman et al. | 502/22 |

OTHER PUBLICATIONS

L. F. Albright et al., "Alkylation of Isobutane with C4 Olefins", 27 *Ind. Eng. Chem. Res.*, 381–397 (1988).
*Handbook of Petroleum Refining Processes* 23–28 (R. A. Meyers, ed., 1986).

*Primary Examiner*—Paul E. Konopka
*Attorney, Agent, or Firm*—Alexander J. McKillop; Dennis P. Santini; Robert B. Furr, Jr.

[57] ABSTRACT

A process is disclosed for regenerating a spent liquid acid catalyst comprising the steps of:

(a) providing a spent liquid acid catalyst comprising HF, sulfolane, and conjunct polymeric byproducts formed during the HF-catalyzed reaction of isoparaffin and olefin to form isoparaffinnic alkylate;

(b) providing a finely divided solid sorbent, wherein said solid sorbent preferentially and reversibly sorbs said conjunct polymeric byproducts from a mixture containing HF, sulfolane;

(c) mixing said spent liquid acid catalyst of step (a) with said solid sorbent of step (b) by charging said spent liquid acid catalyst to the driving fluid inlet of an eductor and drawing a stream containing said solid sorbent into said eductor;

(d) holding said mixture of step (c) in contact for time sufficient for said solid sorbent to preferentially sorb at least a portion of said conjunct polymeric byproducts from said spent liquid acid catalyst to produce a conjunct polymer-enriched sorbent and to regenerate said liquid acid catalyst; and (e) separating said conjunct polymer-enriched sorbent from said regenerated liquid acid catalyst;

(f) soaking said conjunct polymer-enriched sorbent in a solvent to desorb said conjunct polymeric byproducts; and (g) recycling said solid sorbent to said mixing step (c).

15 Claims, 1 Drawing Sheet

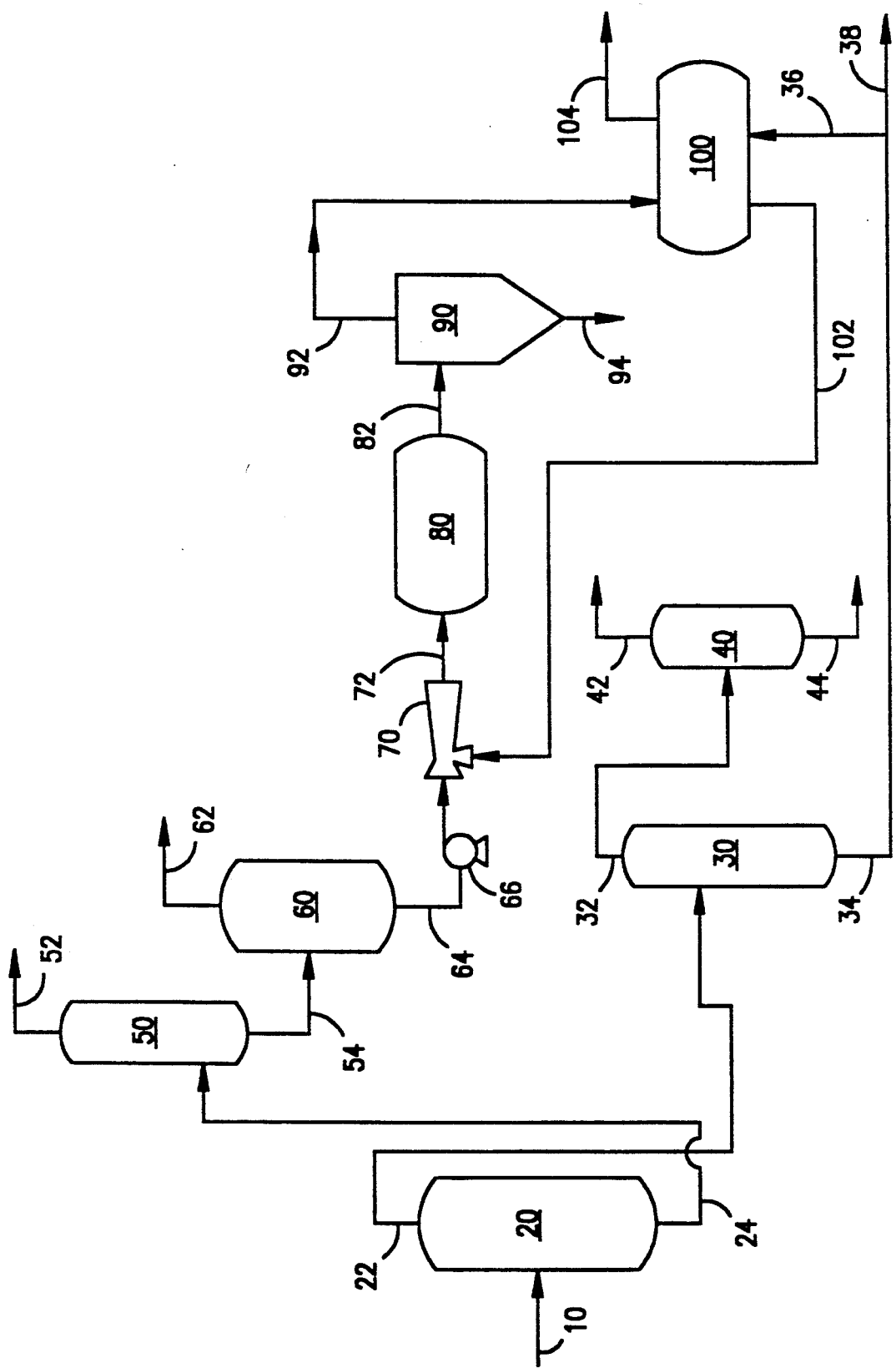

LIQUID ACID REGENERATION METHOD

FIELD OF THE INVENTION

The present invention relates to the art of catalytic alkylation. More specifically, the invention relates to a method for regenerating liquid alkylation catalysts.

BACKGROUND OF THE INVENTION

Alkylation is a reaction in which an alkyl group is added to an organic molecule. For example, an isoparaffin can be reacted with an olefin to provide an isoparaffin of higher molecular weight. In petroleum refining, the process reacts a $C_2$ to $C_5$ olefin with isobutane in the presence of an acidic catalyst to produce an upgraded product stream referred to as alkylate. This alkylate is a valuable blending component in the manufacture of gasolines due not only to its high octane rating but because it is free of aromatic components.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

U.S. Pat. No. 3,795,712 to Torck et al. relates to acid catalysts comprising a Lewis acid, a Bronsted acid, and a sulfone of the formula R—$SO_2$—R', where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,099,924 to Siskin et al. report the use of alkylation catalyst compositions containing HF, a metal halide, and sulfolane. U.S. Pat. No. 5,073,674 to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well as the utility of liquid Bronsted acids in combination with metal halides, particularly metal fluorides.

U.S. Pat. No. 5,191,150 to Child et al. teaches an isoparaffin-olefin alkylation process which addresses the problem of purifying mixtures of HF, sulfolane, and the conjunct polymers (also referred to as acid soluble oil or ASO) formed as byproducts in the HF-catalyzed alkylation of isoparaffins with olefins. The mixture of HF, sulfolane, and ASO (as described in the '150 patent) is difficult to separate because the ASO is a complex mixture of components which boils in a broad range bracketing the boiling point of sulfolane. The entire text of U.S. Pat. No. 5,191,150 is incorporated by reference as if set forth at length herein. For this reason, conventional distillation processes are essentially ineffective for removing ASO from the mixture of HF, sulfolane, and ASO. The process disclosed in the '150 patent first strips the mixture to an HF concentration of 30 weight percent or less, and then gravitationally separates the resulting mixture into an ASO-enriched stream and a sulfolane-enriched stream. Once the HF is stripped from the mixture, however, the process must store and transfer an HF stream containing little or no sulfolane. Thus it would be desirable to provide a method for regenerating an acid catalyst containing HF and sulfolane without stripping the HF from the mixture.

SUMMARY OF THE INVENTION

The present invention provides a process for regenerating a spent acid catalyst containing HF, sulfolane, and ASO. The process of this invention is both safer and simpler to operate than previously known regeneration methods.

The process of the invention comprises the steps of:
(a) providing a spent liquid acid catalyst comprising HF, sulfolane, and conjunct polymeric byproducts formed during the HF-catalyzed reaction of isoparaffin and olefin to form isoparafinnic alkylate;
(b) providing a finely divided solid sorbent having particles with a major dimension of at least about 50 $\mu$m, wherein said solid sorbent preferentially and reversibly sorbs said conjunct polymeric byproducts from a mixture containing HF and sulfolane;
(c) mixing said spent liquid acid catalyst of step (a) with said solid sorbent of step (b) by charging said spent liquid acid catalyst to the driving fluid inlet of an eductor and drawing a stream containing said solid sorbent into said eductor;

(d) holding said mixture of step (c) in contact for time sufficient for said solid sorbent to preferentially sorb at least a portion of said conjunct polymeric byproducts from said spent liquid acid catalyst to produce a conjunct polymer-enriched sorbent and to regenerate said liquid acid catalyst;

(e) separating said conjunct polymer-enriched sorbent from said regenerated liquid acid catalyst;

(f) soaking said conjunct polymer-enriched sorbent in a solvent to desorb said conjunct polymeric byproducts; and (g) recycling said solid sorbent to said mixing step (c).

BRIEF DESCRIPTION OF THE DRAWING

The FIG. is a simplified schematic diagram illustrating the major processing steps in one embodiment of the present invention.

DETAILED DESCRIPTION

The process of this invention regenerates liquid acid catalyst which has become spent by accumulating conjunct polymeric byproducts formed during the isoparaffin-olefin alkylation reaction. In a preferred embodiment, the process uses no mechanical pumping and relies solely upon eduction and downstream pressure drop to transfer fluids and the solid sorbent, and overcomes the equipment reliability problems associated with mechanically pumping a stream containing HF, sulfolane, and a solid sorbent. While not to limit the scope of the invention by a recitation of theory, metals which resist HF attack appear to form a protective film at the metal/solution interface, and maintaining this protective film appears to be critical to controlling corrosion rate. Mechanically pumping a mixture of HF, sulfolane, and a solid sorbent appears to produce flow regimes (particularly in the pump housing and nearby piping) which evidently degrade the protective film formed by the metals of construction. Without the necessary protective surface film, the corrosion rate increases precipitously, causing the equipment to fail prematurely. In contrast, transferring and mixing the fluids and the solid sorbent via eduction and downstream pressure drop in accordance with the present invention causes no such premature equipment failure. Equipment reliability promotes safe and enviromentally responsible process operation in all petroleum refining processes, but is an absolute necessity when handling and storing hazardous materials such as HF. Thus the eduction mixing step and the absence of mechanical pumping in the presence of solid sorbent and HF are critical aspects of the invention and are required for safe and reliable process operation.

The Eduction Mixing Step

The eduction mixing step of the invention overcomes the problems associated with pumping the solid sorbent. The spent liquid acid catalyst containing HF, sulfolane, and conjunct polymeric byproducts (ASO) flows from an operating alkylation process unit and is pumped to a pressure of from about 20 to about 600 psig, preferably from about 40 to about 200 psig, and enters the driving (pumping) fluid inlet of a liquid/liquid eductor. The eductor then draws a mixture of solid sorbent particles and residual desorption solvent from a soaking/desorption vessel into the suction inlet of the eductor and mixes the spent catalyst with the solid sorbent particles and residual desorption solvent.

The liquid/liquid eductor may be of any suitable configuration, and liquid/liquid eductors fabricated from nickel/copper alloys such as Monel brand alloys are preferred. For a discussion of liquid/liquid eductors, see generally R. H. Perry et al., 6 *Chemical Engineers' Handbook* 15 (5th ed., 1973). Eductors are generally taught in U.S. Pat. Nos. 4,815,942 to Alperin et al, 4,898,517 to Eriksen, and 4,960,364 to Tell, which patents are incorporated herein by reference.

The slurry concentration in the soaking/desorption vessel is controlled to provide a flowable slurry and the appropriate desorption solvent concentration in the soaking/desorption vessel may be determined with only minimal trial and error by those skilled in the art.

The Solid Sorbent

The solid sorbents useful in the present invention are macroporous polymers containing substantially nonpolar functional groups. Examples of useful substantially nonpolar functional groups include hydrogen cyanate groups, aromatic groups, and aliphatic groups. Aliphatic substituents having from about 8 to about 18 carbon atoms are preferred, and straight chain aliphatics are still more preferred. The sorbent particles typically range in size (major dimension) from about 30 to about 50$\mu$ or larger. The larger sorbent particles are preferred for ease of separation. One commercially available example of a macroporous polymer sorbent having non-polar hydrocarbon functional groups is available under the tradename Polysorb from Interaction Chemicals, Inc., San Jose, Calif. The density of these macroporous polymeric sorbents typically ranges from about 0.5 to about 0.7 g/cc.

The sorbents preferred for use in the present invention may be described as reverse-phase, as opposed to ionic-phase and normal-phase sorbents. Reverse-phase sorbents having $C_8$ and/or $C_{18}$ substituents are commercially available from the Altech Company of Avondale, Pa., the J. P. Baker Company of Phillipsburg, N.J., and the Baxter Company of McGaw Park, Ill.

Sorption zone temperature and pressure are not critical in the present invention, although the HF/sulfolane/ASO mixture is preferably processed in the liquid phase. Thus the process is compatible with stream temperatures typically found in commercial HF alkylation process units.

Residence time or space velocity is similarly not critical, and solid/liquid contact times as low as 10 seconds or less are acceptable. Longer contact times (lower space velocities) may also be used, but are not necessarily required to effectively sorb ASO from the HF/sulfolane mixture.

The ASO may be desorbed from the solvent by rinsing (or soaking) the sorbent with any suitable solvent, and a nonpolar hydrocarbon solvent such as alkylate is particularly preferred. Normally liquid alkanes such as pentanes and hexanes are also useful desorption solvents. The desorption step preferably comprises a plurality of stages, more preferably three or more stages of countercurrent desorption.

The Sorption/Soaking Step

The solid sorbent must contact the spent liquid acid catalyst for sufficient time to allow the sorbent to selectively sorb the conjunct polymeric byproducts (ASO) from the spent catalyst.

The Solid/Liquid Separation Step

After the solid sorbent has sorbed at least a portion of the conjunct polymeric byproducts (ASO) from the spent catalyst, the sorbent is separated from the now regenerated catalyst and the regenerated catalyst is recycled to the alkylation process unit. The solid sorbent useful in the present invention is less dense than the liquid catalyst. Thus the mixture can be filtered to remove the ASO-enriched solid sorbent, but because the pressure drop across conventional filters increases with solids loading, this option is not preferred. Hydrocyclonic separation is the preferred method for separating the enriched solid sorbent from the regenerated liquid catalyst. Filters may be installed downstream of the hydrocyclone, if desired. Suitable filters include mesh screens, perforated plate, and sintered metal filters. Further, the addition of a filter downstream from the hydrocyclone protects against process unit upsets by assuring liquid product purity even if the flow velocity falls below that required for effective hydrocyclonic separation. In the absence of an auxiliary filter, however, the hydrocyclone should be sized to recover 95–99% or more of the solid component of the alkylation catalyst complex. Specifically, the hydrocyclone should be sized to provide a heavy (sulfolane-rich) stream containing less than 1% weight of solids.

The hydrocyclone separator of the present invention requires a pressure drop of from about 20 to about 150 psig for efficient separation, preferably around about 50 psig. Linear velocities within the hydrocyclone should be kept as low as possible to minimize erosion damage to the hydrocyclone structure. Linear velocities of 70 feet per second or less are preferred, with 50–60 feet per second at a pressure drop of about 25 psi being particularly preferred.

For a survey of design criteria for hydrocyclones, see the four-part series, K. Rietema "Performance and design of hydrocyclones", 15 *Chemical Engineering Science* 298–325, (1961). Examples of hydrocyclones useful in the present invention include those taught in U.S. Pat. Nos. 4,851,134 to Bennoit et al. and 4,960,525 to Dalby et al., which patents are incorporated by reference as if set forth at length herein.

The solids can also be separated from the regenerated liquid catalyst in a holding tank, but this option requires a relatively large sorbent inventory, and is therefore not preferred.

Embodiment

The process embodiment schematically illustrated in the FIGURE treats the reactor effluent stream from an isobutanebutenes alkylation reaction catalyzed by a mixture of HF and sulfolane. Referring now to the FIGURE, the reactor effluent stream 10 flows to gravitational separator 20 where it forms two phases: an upper, less-dense phase enriched in isoparaffinic alkylate and isobutane, and a lower, more-dense phase enriched in HF, sulfolane, and conjunct polymeric byproducts (ASO). The less-dense alkylate-enriched stream 22 withdrawn from the gravitational separator 20 flows to deisobutanizer tower 30 where it separates into an overhead stream 32 enriched in HF and isobutane, and a bottom finished alkylate stream 34. The overhead stream 32 then flows to HF/i-C$_4$ splitter 40 which produces an overhead HF-rich stream 42 and an isobutane-enriched bottom stream 44. The isobutane and HF streams may then be recycled to an alkylation reactor (not shown).

A first portion of the more-dense stream 24 from gravitational separator 20 flows to HF stripper 50, and a second portion flows back to the reactor (not shown). An isobutane stream enters HF stripper 50 near the bottom of the stripper and countercurrently strips HF from the mixture of HF, sulfolane, and ASO. The stripped mixture 54, preferably containing less than about 30 weight percent HF, enters gravitational separator 60 and forms two distinct phases: an upper less-dense phase enriched in ASO, and a bottom stream enriched in sulfolane. The ASO-enriched stream 62 flows to storage facilities (not shown) for additional processing or disposal in accordance with enviromental regulations.

The more-dense sulfolane-enriched stream 64 flows to pump 66 and then flows (as the driving fluid) to eductor 70. A slurry of solid sorbent and finished alkylate 102 flows from soaker/desorber 100 and mixes with sulfolane-enriched stream 64 in eductor 70 to evolve soaker/sorber charge stream 72, which flows to soaker/sorber vessel 80. The mixture of alkylate, solid sorbent, sulfolane, and ASO remains in soaker/sorber vessel 80 for time sufficient for the solid sorbent to preferentially sorb about 30 to 40 weight percent of the ASO present in the soaker/sorber charge stream 72. The effluent mixture 82 from soaker/sorber 80 and enters hydrocyclonic separator 90 where it quickly separates into sulfolane-enriched stream 94 and solid sorbent-containing stream 92. The sulfolane-enriched stream may then be recycled to the alkylation process unit (not shown).

The solid sorbent in stream 92 contains sorbed ASO which must be desorbed before the sorbent can be reused. Stream 92 enters soaker/desorber 100 where it contacts a slip stream 36 of finished alkylate. The ASO readily desorbs from the solid sorbent and the ASO-enriched alkylate 104 may then be distilled (not shown) to recover the alkylate before disposing of the ASO, or the entire stream may be outhauled for disposal.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid are found to separate into two distinct phases more effectively than the stripped mixture containing 30 weight percent hydrofluoric acid.

EXAMPLE 5

The HF/sulfolane sample of Example 5 has the following composition:

| | |
|---|---|
| HF | 62 wt. % |
| Sulfolane | 27 wt. % |
| Isobutane | 4 wt. % |
| Water | 1-2 wt. % |
| ASO | 3 wt. % |

Balance to 100% other hydrocarbons.

This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

EXAMPLE 6

A mixture of about 65 wt. % HF, 30 wt. % sulfolane, and 5 wt. % HF is charged to an acid rerun fractionator at a rate of 58.7 gpm (3.7 l/sec). The ASO/sulfolane stream flows from the bottom of the rerun tower at about 20.6 gpm (1.3 l/sec) and contains approximately 82 wt. % sulfolane, 15 wt. % ASO, and about 3 wt. % HF. This bottom stream (referred to as spent catalyst) is charged to a gravitational separator, where the ASO/sulfolane forms into an ASO-enriched phase containing approximately 87 wt. % ASO, 13 wt. % sulfolane, and the balance HF, which is withdrawn from the gravitational separator at a rate of about 2.1 gpm (0.13 l/sec). The spent catalyst stream is characterized by a specific gravity of about 1.1 g/cm$^3$, and a viscosity ($\mu$) of about 10 cP.

The spent catalyst stream from the gravitational separator is pumped to a pressure of about 150 psig and charged to a liquid/liquid eductor. Sorbent solids comprising a highly cross-linked copolymer with $C_{18}$ and phenyl functional groups and having a density of about 0.6 g/cm$^3$ are drawn into the suction side of the eductor from a low pressure desorption/soaker vessel and mix with the ASO/sulfolane stream.

The mixture of solid sorbent and ASO/sulfolane flows to a soaker vessel where the solid sorbent preferentially sorbs the ASO. The mixture is withdrawn from the soaker vessel and charged to a hydrocyclone having an inside diameter of about 3.1 inches (8 cm) and a vortex diameter of about 1 inch (2.5 cm). The liquid stream recovered from the hydrocyclone contains less than 0.5 wt. % ASO and the solid sorbent, enriched in ASO, is charged to a soaker/regenerator to desorb the ASO with alkylate gasoline before recycling the solid sorbent to the eductor.

EXAMPLE 7

A spent liquid alkylation catalyst (21.92 parts by weight containing 6.32 wt. % ASO, 88.28 wt. % sulfolane, and 5.4 wt. % HF) is mixed with a reverse-phase sorbent (2.09 parts by weight, MP-1 SPE brand sorbent commercially available from the Alltech Company of Avondale, Pa.). After separation, the sulfolane-rich phase contains 91.9 wt. % sulfolane, 2.8 wt. % ASO, and 5.4 wt. % HF. These results show that the sorbent sorbs 0.783 parts ASO (or 38% of the weight of the sorbent).

Changes and modifications in the specifically described embodiments can be carried out without departing from the scope of the invention which is intended to be limited only by the scope of the appended claims.

What is claimed is:

1. A process for regenerating a spent liquid acid catalyst comprising the steps of:
   (a) providing a spent liquid acid catalyst comprising HF, sulfolane, and conjunct polymeric byproducts formed during the HF-catalyzed reaction of isoparaffin and olefin to form isoparafinnic alkylate;
   (b) providing a finely divided solid sorbent, wherein said solid sorbent preferentially and reversibly sorbs said conjunct polymeric byproducts from a mixture containing HF and sulfolane;
   (c) mixing said spent liquid acid catalyst of step (a) with said solid sorbent of step (b) by charging said spent liquid acid catalyst to the driving fluid inlet of an eductor and drawing a stream containing said solid sorbent into said eductor;
   (d) holding said mixture of step (c) in contact for time sufficient for said solid sorbent to preferentially sorb at least a portion of said conjunct polymeric byproducts from said spent liquid acid catalyst to produce a conjunct polymer-enriched sorbent and to regenerate said liquid acid catalyst; and
   (e) separating said conjunct polymer-enriched sorbent from said regenerated liquid acid catalyst;
   (f) soaking said conjunct polymer-enriched sorbent in a solvent to desorb said conjunct polymeric byproducts; and
   (g) recycling said solid sorbent to said mixing step (c).

2. The process of claim 1 wherein said solvent of step (f) comprises an isoparaffin.

3. The process of claim 2 wherein said solvent comprises the alkylate product of at least one olefin and at least one isoparaffin.

4. The process of claim 1 wherein said solid sorbent comprises a reverse-phase sorbent.

5. The process of claim 1 wherein said solid sorbent comprises a cross-linked macroporous polymer containing substantially non-polar substituent groups.

6. The process of claim 5 wherein said solid sorbent comprises particles having a major dimension of at least about 50 μm.

7. The method of claim 1 further comprising the sequential steps of
   (h) separating hydrofluoric acid from said spent liquid acid catalyst prior to said mixing step (c) to provide an intermediate stream containing less than about 30 percent hydrofluoric acid by weight;
   (i) gravitationally separating said intermediate stream of step (h) into a sulfolane-enriched stream and a conjunct polymer-enriched stream; and
   (j) charging said sulfolane-enriched stream to said mixing step (c).

8. The method of claim 7 wherein said hydrofluoric acid is separated from said mixture by stripping.

9. The method of claim 8 wherein said stripping fluid comprises an isoparaffin.

10. The method of claim 8 wherein said stripping step comprises sequentially stripping said mixture with isoparaffin and then stripping said mixture with nitrogen.

11. The method of claim 7 wherein said hydrofluoric acid separation step provides an intermediate stream containing less than about 25 percent hydrofluoric acid by weight.

12. The method of claim 11 wherein said hydrofluoric acid separation step provides an intermediate stream containing less than about 10 percent hydrofluoric acid by weight.

13. The method of claim 12 wherein said hydrofluoric acid separation step provides an intermediate stream containing less than about 5 percent hydrofluoric acid by weight.

14. The method of claim 1 wherein said separation step (e) further comprises separating said polymer-enriched sorbent and said liquid acid catalyst of step (d) in a hydrocyclone.

15. The method of claim 7 wherein said separation step (e) further comprises separating said polymer-enriched sorbent and said liquid acid catalyst of step (d) in a hydrocyclone.

* * * * *